US012668561B2

(12) United States Patent
Miyake et al.

(10) Patent No.: US 12,668,561 B2
(45) Date of Patent: Jun. 30, 2026

(54) PROCESS FOR PREPARING (Z)-7-TETRADECEN-2-ONE

(71) Applicant: Shin-Etsu Chemical Co., Ltd., Tokyo (JP)

(72) Inventors: Yuki Miyake, Joetsu (JP); Takeru Watanabe, Joetsu (JP); Ryo Komatsu, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 478 days.

(21) Appl. No.: 18/502,238

(22) Filed: Nov. 6, 2023

(65) Prior Publication Data

US 2024/0182394 A1 Jun. 6, 2024

(30) Foreign Application Priority Data

Nov. 10, 2022 (JP) ................................ 2022-180404

(51) Int. Cl.

| | |
|---|---|
| ***C07C 45/29*** | (2006.01) |
| ***C07C 17/275*** | (2006.01) |
| ***C07C 17/354*** | (2006.01) |
| ***C07C 45/78*** | (2006.01) |
| ***C07C 49/203*** | (2006.01) |
| ***C07C 67/42*** | (2006.01) |

(52) U.S. Cl.

CPC ............ *C07C 45/29* (2013.01); *C07C 17/275* (2013.01); *C07C 17/354* (2013.01); *C07C 45/78* (2013.01); *C07C 49/203* (2013.01); *C07C 67/42* (2013.01)

(58) Field of Classification Search

CPC ....... C07C 45/27; C07C 45/29; C07C 49/203; C07C 17/354; C07C 12/04; C07C 29/36; C07C 33/025

See application file for complete search history.

(56) References Cited

FOREIGN PATENT DOCUMENTS

| | | | | | |
|---|---|---|---|---|---|
| JP | 2000229962 A | * | 8/2000 | ............. | C07C 45/39 |
| JP | 2003206254 A | * | 7/2003 | ............. | C07B 61/00 |
| JP | 2004300111 A | * | 10/2004 | ............. | C07C 45/34 |
| JP | 2008143865 A | * | 6/2008 | ............. | C07C 45/62 |

OTHER PUBLICATIONS

Hong, Y.P., et al., Efficient synthetic method for oriental beetle sex pheromone, (Z)-7-7tetradecen-2-one, Department of Applied Chemistry, Andong National University, Journal of the Korean Chemical Society,57(6), pp. 865-868 (Year: 2013).*

Koppenhofer et al. "Mating Disruption of Oriental Beetle (Coleoptera: Scarabaeidae) in Turfgrass Using Microencapsulated Formulations of Sex Pheromone Components" Environmental Entomology, 34(6):1408-1417 (2005).

Leal, W.S. "(Z)- and (E)-Tetradec-7-en-2-one, a New Type of Sex Pheromone from the Oriental Beetle" Naturwissenschaften, 80(2):86-87 (1993).

Rodriguez-Saona et al. "Optimization of Pheromone Deployment for Effective Mating Disruption of Oriental Beetle (Coleoptera: Scarabaeidae) in Commercial Blueberries" Journal of Economic Entomology, 102(2):659-669 (2009).

* cited by examiner

*Primary Examiner* — Yate' K Cutliff
(74) *Attorney, Agent, or Firm* — Myers Bigel, P.A.

(57) ABSTRACT

The present invention relates to a process for preparing (Z)-7-tetradecen-2-one of the following formula (5), the process comprising the steps of converting a (Z)-1-halo-4-undecene compound (1) of the following general formula (1), wherein $X^1$ represents a halogen atom, into a nucleophilic reagent, (Z)-4-undecenyl compound, of the following general formula (2), wherein $M^1$ represents Li or $MgZ^1$, and $Z^1$ represents a halogen atom or a (4Z)-4-undecenyl group, subjecting the nucleophilic reagent, (Z)-4-undecenyl compound (2), to an addition reaction with propylene oxide of the following formula (3) to obtain (Z)-7-tetradecen-2-ol of the following formula (4) and oxidizing (Z)-7-tetradecen-2-ol (4) thus obtained to form (Z)-7-tetradecen-2-one (5).

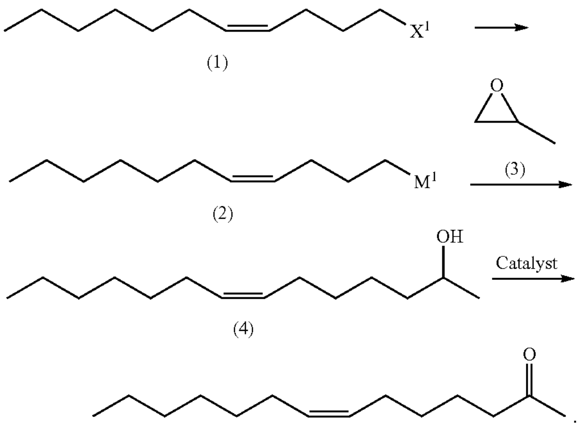

(1)
(2)
(4)
(5)

10 Claims, No Drawings

PROCESS FOR PREPARING (Z)-7-TETRADECEN-2-ONE

TECHNICAL FIELD

The present invention relates to a process for preparing (Z)-7-tetradecen-2-one, the sex pheromone of the Oriental beetle (scientific name: *Anomala orientalis*).

BACKGROUND ART

The Oriental beetle is one of the most serious pests of blueberry trees in the United States. Larvae of the Oriental beetle feed on the roots of blueberry trees, thereby reducing the vitality of the trees and consequently reducing the fruit yield. Moreover, blueberry trees may wither and die if the density of the Oriental beetle is high and the feeding damage is severe. Although pesticides, such as imidacloprid, have been used to control the Oriental beetle, not only is it difficult to know the proper timing for applying pesticides because the Oriental beetle burrows underground except during the adult stage, but imidacloprid is undesirable due to its adverse effects on honeybees. Hence, efforts have been focused on sex pheromone lures used to identify pest outbreaks so that pesticide spraying can be performed only when necessary, as well as biological control methods that reduce the use of pesticides as much as possible. Mating disruption by means of sex pheromones is one promising biological control method (Non-Patent Literatures 1 and 2 below).

The sex pheromone of the Oriental beetle is reported to be a 7:1 mixture of (Z)-7-tetradecen-2-one and (E)-7-tetradecen-2-one (Non-Patent Literature 3 below).

A process for synthesizing (Z)-7-tetradecen-2-one is reported (Non-Patent Literature 3 below) in which, for example, 1-octynyllithium and 1,4-dibromobutane are reacted in a mixed solvent of tetrahydrofuran and hexamethylphosphoric triamide (HMPA) to synthesize 1-bromo-5-decyne. 1-Bromo-5-decyne is then subjected to a reduction reaction in the presence of a palladium-barium sulfate catalyst in a methanol solvent to synthesize 1-bromo-5-decene. 1-Bromo-5-decene thus obtained is then converted into a Grignard reagent, followed by subjecting the Grignard reagent to an addition reaction with acetic anhydride to obtain (Z)-7-tetradecen-2-one.

Another process for synthesizing (Z)-7-tetradecen-2-one is reported (Patent Literature 1 below) in which, for example, 1-octynyllithium and 1,3-dibromopropane are reacted in a mixed solvent of tetrahydrofuran and hexamethylphosphoric triamide (HMPA) to synthesize 1-bromo-4-undecyne. An acetoacetic ester synthesis reaction of ethyl acetoacetate (ethyl 3-oxobutanoate) and the aforesaid 1-bromo-4-undecyne is then carried out in dimethyl sulfoxide (DMSO) in the presence of sodium hydride as a base to synthesize 3-ethoxycarbonyl-7-tetradecyn-2-one. 3-Ethoxycarbonyl-7-tetradecyn-2-one thus obtained is then subjected to alkali hydrolysis in a mixed solvent of potassium hydroxide, methanol, and water, followed by decarboxylation to synthesize 7-tetradecyn-2-one. 7-Tetradecyn-2-one thus obtained is then subjected to a catalytic hydrogenation reaction with hydrogen in a methanol solvent in the presence of palladium-barium sulfate as a catalyst and quinoline as a catalyst poison to obtain (Z)-7-tetradecen-2-one. A calculation of the yield of (Z)-7-tetradecen-2-one in Patent Literature 1 based on the statement of an example of Patent Literature 1 that "(Z)-7-tetradecen-2-one can be prepared with a purity of 95% or more by performing purification by distillation in the first step and without performing purification in the second to fourth steps" gives an estimated yield of 46.53% for the four steps.

PRIOR ART

Non-Patent Literatures

[Non-Patent Literature 1] Albrecht M. Koppenhofer et al., Environ. Entomol., 2005, 34 (6), 1408-1417.

[Non-Patent Literature 2] Cesar R. Rodriguez-Saona et al., J. Econ. Entomol., 2009, 102 (2), 659-669.

[Non-Patent Literature 3] W. S. Leal et al., Naturwissenschaften, 1993, 80, 86-87.

Patent Literature

[Patent Literature 1] Japanese Patent Application Laid-Open No. 2008-143865.

OBJECT OF THE INVENTION

However, the processes for synthesizing (Z)-7-tetradecen-2-one of Non-Patent Literature 3 and Patent Literature 1 are not industrially practical due to the use of expensive palladium catalysts, and are unsafe due to the use of large amounts of hexamethylphosphoric triamide, a carcinogen, as a solvent. Moreover, the preparation process of Patent Literature 1 is not industrially practical due to the use of ignitable sodium hydride, and is undesirable in view of quality control because impurities undetectable by gas chromatography may be contaminated in the second to fourth step that lack purification as described by the inventors of Patent Literature 1.

The present invention has been made in view of the aforementioned circumstances, and aims to provide an industrially practical process for efficiently preparing (Z)-7-tetradecen-2-one with fewer steps.

SUMMARY OF THE INVENTION

As a result of intensive research to overcome the aforesaid problems of the prior art, the present inventors found that a (Z)-1-halo-4-undecene compound is a useful intermediate in the preparation of (Z)-7-tetradecen-2-one (5), the sex pheromone of the Oriental beetle. The present inventors further found that the (Z)-1-halo-4-undecene compound can be used to industrially and efficiently prepare the aforesaid (Z)-7-tetradecen-2-one with fewer steps, and thus have completed the present invention.

According to a first aspect of the present invention, there is provided a process for preparing (Z)-7-tetradecen-2-one of the following formula (5):

(5)

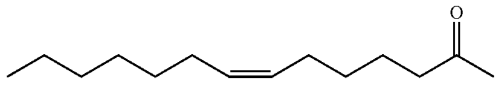

the process comprising the steps of:

converting a (Z)-1-halo-4-undecene compound (1) of the following general formula (1):

(1)

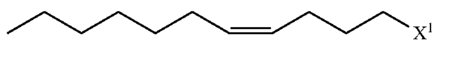

wherein $X^1$ represents a halogen atom, into a nucleophilic reagent, (Z)-4-undecenyl compound, of the following general formula (2):

(2)

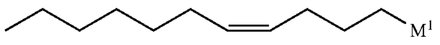

wherein $M^1$ represents Li or $MgZ^1$, and $Z^1$ represents a halogen atom or a (4Z)-4-undecenyl group, subjecting the nucleophilic reagent, (Z)-4-undecenyl compound (2), to an addition reaction with propylene oxide of the following formula (3):

(3)

to obtain (Z)-7-tetradecen-2-ol of the following formula (4):

(4)

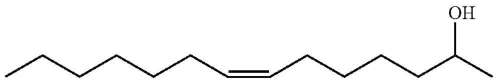

and oxidizing (Z)-7-tetradecen-2-ol (4) thus obtained to form (Z)-7-tetradecen-2-one (5).

According to a second aspect of the present invention, there is provided a process for preparing (Z)-7-tetradecen-2-one (5), wherein the aforesaid oxidization process according to the first aspect is carried out by an Oppenauer oxidation.

According to a third aspect of the present invention, there is provided a process for preparing (Z)-7-tetradecen-2-one (5), comprising obtaining the aforesaid (Z)-7-tetradecen-2-one (5) according to the first or second aspect, the process further comprising:

esterifying the (Z)-7-tetradecen-2-ol (4) remaining after the aforesaid step of obtaining (Z)-7-tetradecen-2-one (5) according to the first or second aspect, wherein the esterification makes possible purification of the aforesaid (Z)-7-tetradecen-2-one (5), a target compound, from a reaction mixture after the aforesaid step of the esterification.

According to a fourth aspect of the present invention, there is provided a process for preparing (Z)-7-tetradecen-2-one (5), comprising the aforesaid step of esterification according to the third aspect, the process further comprising the step of:

purifying (Z)-7-tetradecen-2-one (5) from a reaction mixture of (Z)-7-tetradecen-2-one (5) and an esterified product of (Z)-7-tetradecen-2-ol (4) after the aforesaid step of esterification.

A fifth aspect of the present invention comprises the aforesaid process for preparing (Z)-7-tetradecen-2-one (5) according to the first to fourth aspects, the process further comprising the step of:

subjecting a 1-halo-4-undecyne compound of the following general formula (6):

(6)

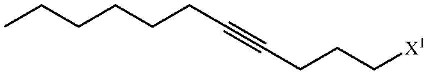

wherein $X^1$ represents a halogen atom, to a reduction reaction to obtain the (Z)-1-halo-4-undecene compound (1).

A sixth aspect of the present invention comprises the aforesaid process for preparing (Z)-7-tetradecen-2-one (5) according to the fifth aspect, the process further comprising:

subjecting a nucleophilic reagent, hexyl compound, of the following general formula (7):

(7)

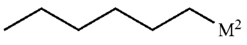

wherein $M^2$ represents Li or $MgZ^2$, and $Z^2$ represents a halogen atom or a hexyl group, to a coupling reaction with a 1,5-dihalo-1-pentyne compound of the following general formula (8):

(8)

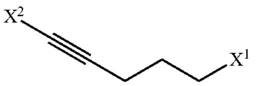

wherein $X^1$ and $X^2$ represent, independently of each other, a halogen atom, to form 1-halo-4-undecyne (6).

According to the present invention, (Z)-7-tetradecen-2-one can be industrially prepared efficiently with good yield and fewer steps, without using dangerous compounds such as carcinogens or dangerous reactions with ignitable sodium hydride. According to the present invention, a useful synthetic intermediate for preparing (Z)-7-tetradecen-2-one also can be provided.

DETAILED DESCRIPTION OF THE INVENTION

A. (Z)-1-halo-4-undecene Compound of Following General Formula (1)

(1)

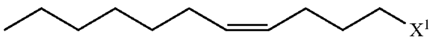

In the general formula (1), $X^1$ represents a halogen atom.

Specifically, examples of the halogen atom, $X^1$, include a chlorine atom, a bromine atom, and an iodine atom. A chlorine atom and a bromine atom are preferred, and a chlorine atom is particularly preferred. By using said chlorine atom and bromine atom, a preferable availability may be ensured. By using said chlorine atom, a particularly preferable availability may be ensured.

Specific examples of the (Z)-1-halo-4-undecene compound (1) include (Z)-1-chloro-4-undecene, (Z)-1-bromo-4-undecene, and (Z)-1-iodo-4-undecene.

The (Z)-1-halo-4-undecene compound (1) may be prepared according to, for example, the following chemical reaction formula.

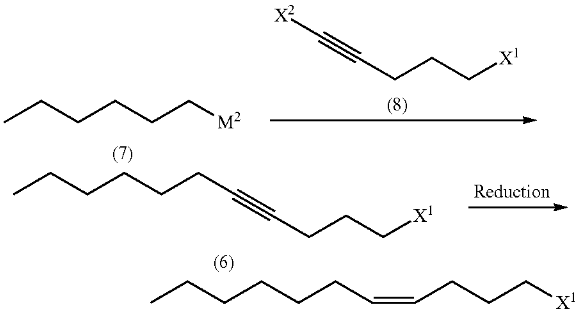

(7)

(6)

(1)

First, a nucleophilic reagent, hexyl compound, of the general formula (7) is subjected to a coupling reaction with a 1,5-dihalo-1-pentyne compound of the general formula (8) to prepare a 1-halo-4-undecyne compound of the general formula (6). The aforesaid (Z)-1-halo-4-undecene compound (1) may be prepared by subjecting the 1-halo-4-undecyne compound (6) to a reduction reaction.

Next, a specific process for preparing the (Z)-1-halo-4-undecene compound (1) will be explained below in Section B and Section C.

B. Process for Preparing 1-halo-4-undecyne Compound (6) by Coupling Reaction of Nucleophilic Reagent, Hexyl Compound (7), and 1,5-dihalo-1-pentyne Compound (8)

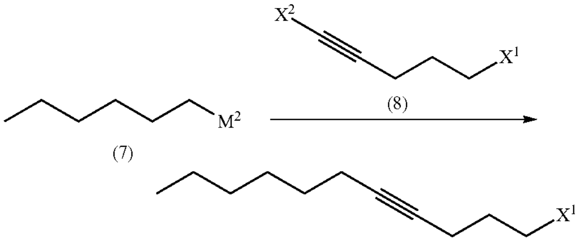

(7)

(6)

B-1. 1-Halo-4-undecyne Compound (6)

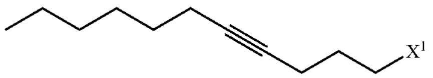

(6)

In the general formula (6), $X^1$ represents a halogen atom.

Specifically, examples of the halogen atom, $X^1$, include a chlorine atom, a bromine atom, and an iodine atom. A chlorine atom and a bromine atom are preferred, and a chlorine atom is particularly preferred. By using said chlorine atom and bromine atom, a preferable availability may be ensured. By using said chlorine atom, a particularly preferable availability may be ensured.

Specific examples of the 1-halo-4-undecyne compound (6) include 1-chloro-4-undecyne, 1-bromo-4-undecyne, and 1-iodo-4-undecyne.

B-2. Coupling Reaction of Nucleophilic Reagent, Hexyl Compound (7), and 1,5-dihalo-1-pentyne Compound (8)

B-2-1. 1,5-dihalo-1-pentyne Compound (8)

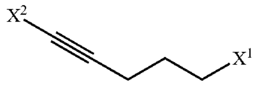

(8)

In the general formula (8), $X^1$ and $X^2$ represent, independently of each other, a halogen atom.

Specifically, examples of the halogen atoms, $X^1$ and $X^2$, include a chlorine atom, a bromine atom, and an iodine atom. $X^1$ is preferably a chlorine atom and a bromine atom, and more preferably a chlorine atom. By using said chlorine atom and bromine atom, a preferable reactivity may be ensured. By using said chlorine atom, a more preferable reactivity may be ensured. $X^2$ is preferably a bromine atom and an iodine atom, and more preferably a bromine atom. By using said bromine atom and iodine atom, a preferable reactivity may be ensured. By using said bromine atom, a more preferred reactivity may be ensured. In preferred combinations of $X^1$ and $X^2$, $X^2$ is preferably a chlorine atom, a bromine atom, or an iodine atom when $X^1$ is a chlorine atom; and $X^2$ is preferably a bromine atom or an iodine atom when $X^1$ is a bromine atom.

Specific examples of the 1,5-dihalo-1-pentyne compound (8) include 1,5-dichloro-1-pentyne, 1,5-dibromo-1-pentyne, 1,5-diiodo-1-pentyne, 5-bromo-1-chloro-1-pentyne, 1-chloro-5-iodo-1-pentyne, 1-bromo-5-chloro-1-pentyne, 1-bromo-5-iodo-1-pentyne, 5-chloro-1-iodo-1-pentyne, and 5-bromo-1-iodo-1-pentyne. 1,5-Dichloro-1-pentyne, 1,5-dibromo-1-pentyne, 1-bromo-5-chloro-1-pentyne, 5-chloro-1-iodo-1-pentyne, and 5-bromo-1-iodo-1-pentyne are preferred, and 1,5-dibromo-1-pentyne, 1-bromo-5-chloro-1-pentyne, and 5-chloro-1-iodo-1-pentyne are more preferred. By using said 1,5-dichloro-1-pentyne, 1,5-dibromo-1-pentyne, 1-bromo-5-chloro-1-pentyne, 5-chloro-1-iodo-1-pentyne, and 5-bromo-1-iodo-1-pentyne, a preferable reactivity may be ensured. By using said 1,5-dibromo-1-pentyne, 1-bromo-5-chloro-1-pentyne, and 5-chloro-1-iodo-1-pentyne, a more preferred reactivity may be ensured.

The 1,5-dihalo-1-pentyne compound (8) may be used alone or in combination thereof, if necessary. The 1,5-dihalo-1-pentyne compound (8) may be a commercially available one or may be synthesized in house.

B-2-2. Nucleophilic Reagent, Hexyl Compound (7):

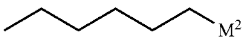

(7)

In the general formula (7), $M^2$ represents Li or $MgZ^2$, and $Z^2$ represents a halogen atom or a hexyl group.

Specifically, examples of the halogen atom include a chlorine atom, a bromine atom, and an iodine atom. A chlorine atom and a bromine atom are preferred, and a chlorine atom is particularly preferred. By using said chlorine atom and bromine atom, a preferable availability may be ensured. By using said chlorine atom, a particularly preferable availability may be ensured.

Specific examples of the nucleophilic reagent, hexyl compound (7), include hexyllithium; and hexylmagnesium halide compounds such as hexylmagnesium chloride, hexylmagnesium bromide, and hexylmagnesium iodide.

The amount of the nucleophilic reagent, hexyl compound (7), used in the coupling reaction is preferably 0.6 to 2.0 mol, and more preferably 0.8 to 1.4 mol, per mol of the 1,5-dihalo-1-pentyne compound (8). By using said preferred amount and said more preferred amount, a preferable reactivity and a more preferred reactivity may be ensured.

The nucleophilic reagent, hexyl compound (7), may be used alone or in combination thereof, if necessary. The nucleophilic reagent, hexyl compound (7), may be a commercially available one or may be synthesized in house.

A solvent may be incorporated in the coupling reaction, if necessary. Examples of the solvent include general solvents such as, for example, ether solvents such as tetrahydrofuran (THF), 2-methyltetrahydrofuran (2-MeTHF), diethyl ether, dibutyl ether, 4-methyltetrahydropyran (MTHP), cyclopentylmethylether, and 1,4-dioxane; hydrocarbon solvents such as hexane, heptane, benzene, toluene, xylene, and cumene; and polar solvents such as N,N-dimethylformamide (DMF), N,N-dimethylacetamide (DMAC), N-methylpyrrolidone (NMP), dimethyl sulfoxide (DMSO), γ-butyrolactone (GBL), acetonitrile, N,N'-dimethylpropylene urea (DMPU), hexamethylphosphoric triamide (HMPA), dichloromethane, and chloroform. Hydrocarbon solvents such as toluene and xylene; and ether solvents such as tetrahydrofuran, 2-methyltetrahydrofuran, 4-methyltetrahydropyran, and diethyl ether are preferred, and tetrahydrofuran, 2-methyltetrahydrofuran, toluene, and xylene are more preferred. By using said hydrocarbon solvents such as toluene and xylene; and ether solvents such as tetrahydrofuran, 2-methyltetrahydrofuran, 4-methyltetrahydropyran, and diethyl ether, a preferable reactivity may be ensured. By using said tetrahydrofuran, 2-methyltetrahydrofuran, toluene, and xylene, a more preferred reactivity may be ensured.

The solvent may be used alone or in combination thereof, if necessary. The solvent may be a commercially available one.

The amount of the solvent used is preferably 30 to 8,000 g, and more preferably 50 to 5,000 g, per mol of the 1,5-dihalo-1-pentyne compound (8). By using said preferred amount and said more preferred amount, a preferable reactivity and a more preferred reactivity may be ensured.

A catalyst may be used to subject the nucleophilic reagent, hexyl compound (7), to a coupling reaction with the 1,5-dihalo-1-pentyne compound (8), if necessary.

Examples of the catalyst include copper compounds such as cuprous halides such as cuprous chloride, cuprous bromide, and cuprous iodide, and cupric halides such as cupric chloride, cupric bromide, and cupric iodide; iron compounds such as iron(II) chloride, iron(III) chloride, iron(II) bromide, iron(III) bromide, iron(II) iodide, iron(III) iodide, and iron (III) acetylacetonate; silver compounds such as silver chloride, silver nitrate, and silver acetate; titanium compounds such as titanium tetrachloride, titanium tetrabromide, titanium(IV) methoxide, titanium(IV) ethoxide, titanium(IV) isopropoxide, and titanium(IV) oxide; palladium(II) compounds such as dichlorobis(triphenylphosphine)palladium and dichloro[1,1'-bis(diphenylphosphino)ferrocene]palladium; and nickel compounds such as nickel chloride, dichloro[1,2-bis(diphenylphosphino)ethane]nickel(II), and dichlorobis(triphenylphosphine)nickel(II). Copper compounds are preferred, and cupric halides such as cupric chloride, cupric bromide, and cupric iodide are more preferred. By using said copper compounds, a preferable reactivity and/or economy may be ensured. By using said cupric halides such as cupric chloride, cupric bromide, and cupric iodide, a more preferred reactivity and/or economy may be ensured.

The catalyst may be used alone or in combination thereof, if necessary. The catalyst may be a commercially available one.

The amount of the catalyst used is preferably 0.0001 to 1.00 mol, and more preferably 0.001 to 0.300 mol, per mol of the 1,5-dihalo-1-pentyne compound (8). By using said preferred amount and said more preferred amount, a preferable reaction rate and post-processing and a more preferred reaction rate and post-processing may be ensured.

When the coupling reaction is carried out in the presence of a catalyst, a co-catalyst may be used, if necessary. Examples of the co-catalyst include trialkyl phosphite compounds having 3 to 9 carbon atoms such as triethyl phosphite; and arylphosphine compounds having 18 to 44 carbon atoms such as triphenylphosphine, tritolylphosphine, and 2,2'-bis(diphenylphosphino)-1,1'-binaphthyl (BINAP). The co-catalyst is preferably trialkyl phosphite, and particularly preferably triethyl phosphite. By using said trialkyl phosphite and said triethyl phosphite, a preferable reactivity and a particularly preferred reactivity may be ensured.

The co-catalyst may be used alone or in combination thereof, if necessary. The co-catalyst may be a commercially available one.

The amount of the co-catalyst used is preferably 0.0001 to 1.00 mol, and more preferably 0.001 to 0.300 mol, per mol of the 1,5-dihalo-1-pentyne compound (8).

A lithium salt may be added when the coupling reaction is carried out in the presence of a catalyst, if necessary. Examples of the lithium salt include lithium halides such as lithium chloride, lithium bromide, and lithium iodide, lithium nitrate, and lithium carbonate. The lithium salt is preferably lithium chloride, lithium bromide, lithium iodide, and lithium nitrate, and particularly preferably lithium chloride. By using said lithium chloride, lithium bromide, lithium iodide, and lithium nitrate, a preferable reactivity may be ensured. By using said lithium chloride, a particularly preferred reactivity may be ensured.

The lithium salt may be used alone or in combination thereof, if necessary. The lithium salt may be a commercially available one.

The amount of the lithium salt used in the coupling reaction is preferably 0.0001 to 1.00 mol, and more preferably 0.001 to 0.300 mol, per mol of the 1,5-dihalo-1-pentyne compound (8). By using said preferred amount and said more preferred amount, a preferable reactivity and a more preferred reactivity may be ensured.

The reaction temperature of the coupling reaction varies, depending on the nucleophilic reagent, hexyl compound (7), to be used, and is preferably −78 to 100° C., and more preferably −25 to 60° C. By using said preferred reaction temperature and said more preferred reaction temperature, a preferable reactivity and a more preferred reactivity may be ensured.

The reaction time of the coupling reaction varies, depending on the solvent and/or the production scale to be used, and is preferably 0.5 to 100 hours. By using said reaction time, a preferable reactivity may be ensured.

C. Process for Preparing (Z)-1-halo-4-undecene Compound (1) by Subjecting 1-halo-4-undecyne Compound (6) to Reduction Reaction

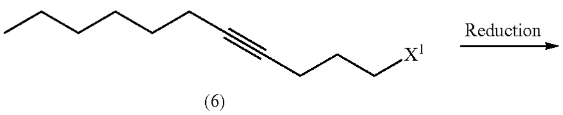

(6)

-continued

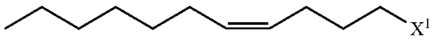

(1)

Reduction Reaction

Examples of a reduction reaction in which the carbon-carbon triple bond of the 1-halo-4-undecyne compound (6) is reduced to form the (Z)-1-halo-4-undecene compound (1) include (i) a catalytic hydrogenation reaction, (ii) a reduction reaction with a zinc compound in an alcohol solvent, (iii) a hydroboration with dialkylborane, followed by a reduction reaction by protonation, (iv) a reduction reaction with potassium hydroxide and N,N-dimethylformamide (DMF) in the presence of a palladium catalyst such as palladium acetate, and (v) hydrosilylation to obtain vinylsilane followed by a reduction reaction to desilylate. (i) The catalytic hydrogenation reaction, (ii) the reduction reaction with the zinc compound, and (iii) the hydroboration, followed by the reduction reaction by protonation, are preferred, and (i) the catalytic hydrogenation reaction is more preferred. By using said (i) catalytic hydrogenation reaction, (ii) reduction reaction with the zinc compound, and (iii) hydroboration, followed by the reduction reaction by protonation, a preferable selectivity and ease of preparation may be ensured. By using said (i) catalytic hydrogenation reaction, a more preferred selectivity and ease of preparation may be ensured.

(i) Catalytic Hydrogenation Reaction

The catalytic hydrogenation reaction is carried out with a hydrogen gas in the presence of a metal catalyst.

Examples of the metal catalyst used in the catalytic hydrogenation reaction include, but are not limited to, nickel catalysts such as a nickel boride catalyst, nickel(0) nanoparticles (Fransisco Alonso et al., Tetrahedron, 2007, 63, 93-102), and Urushibara nickel (for example, U-Ni-A and U-Ni-B); and palladium catalysts such as a Lindlar catalyst, palladium on carbon, $Pd/CaCO_3$, $Pd/BaSO_4$, $Pd/Al_2O_3$, $Pd/SiO_2$ doped with Hg, Pd/McM-41, Pd nanoparticles in hydrotalcite, Pd/Zn alloy, and Pd-PEI which is palladium on carbon poisoned with a polyethylenimine polymer (PEI). Examples of the nickel boride catalyst include, but are not limited to, a P-1 nickel boride catalyst and a P-2 nickel boride catalyst (Thomas J. Caggiano et al., Encyclopedia of Reagents for Organic Synthesis: 3694-3699) (hereinafter, also referred to as “P-2 Ni catalyst”); and dispersed nickel on graphite (for example, Ni-Gr1 and Ni-Gr2), a Caubere catalyst (Nic), and nickel on a borohydride exchange resin ($Ni_2B$-BER) (Laurence Balas, HAL, 2021; <https://hal.archives-ouvertes.fr/hal-00801666>). The Lindlar catalyst and the nickel catalysts are preferred. By using said Lindlar catalyst and nickel catalysts, preferable economy may be ensured.

The amount of the metal catalyst used varies, depending on the catalyst to be used, and is preferably 0.01 to 50 g, per mol of the 1-halo-4-undecyne compound (6) when a solid catalyst such as the Lindlar catalyst is used. By using said amount, a preferable reactivity may be ensured. When a liquid catalyst such as a P-2 Ni catalyst is used, the amount of the catalyst used is preferably an amount equivalent to 0.0001 to 2.0 mol of a nickel compound, per mol of the 1-halo-4-undecyne compound (6).

A solid catalyst may be dispersed in a solvent.

When the metal catalyst has high activity, a catalyst poison may be used, if necessary.

Examples of the catalyst poison include amine compounds such as pyridine, quinoline, and ethylenediamine; phosphine compounds such as triphenyiphosphine, tritolyiphosphine, and triethyl phosphite; and sulfur compounds such as benzenethiol, diphenyl sulfide, dimethyl sulfide, and dimethyl sulfoxide.

The amount of the catalyst poison used varies, depending much on the catalyst poison to be used, and is preferably 0.0001 to 20.0 mol, and more preferably 0.001 to 2.0 mol, per mol of the 1-halo-4-undecyne compound (6). By using said preferred amount and said more preferred amount, a preferable reaction rate and geometrical selectivity and a more preferred reaction rate and geometrical selectivity may be ensured.

Examples of the solvent used in the catalytic hydrogenation reaction include hydrocarbon solvents such as hexane, heptane, benzene, toluene, xylene, and cumene; nitriles such as acetonitrile and propionitrile; esters such as methyl acetate, ethyl acetate, n-propyl acetate, and n-butyl acetate; and alcohols such as methanol, ethanol, propanol, butanol, pentanol, hexanol, 2-propanol, 2-butanol, and cyclohexanol.

The solvent may be used alone or in combination thereof, if necessary. The solvent may be a commercially available one.

When a Lindlar catalyst is used, the solvent is preferably hydrocarbon solvents such as hexane, heptane, toluene, and xylene. By using said hydrocarbon solvents such as hexane, heptane, toluene, and xylene, a preferable reactivity may be ensured. When a nickel catalyst is used, the solvent is preferably alcohols such as methanol, ethanol, propanol, butanol, and 2-propanol. By using said alcohols such as methanol, ethanol, propanol, butanol, and 2-propanol, a preferable reactivity may be ensured. When a palladium catalyst such as palladium on carbon is used, the solvent is preferably esters such as methyl acetate and ethyl acetate. By using said esters such as methyl acetate and ethyl acetate, a preferable reactivity may be ensured.

The amount of the solvent used varies, depending on the catalyst and/or the solvent to be used, and is preferably 0 to 1,000 g, per mol of the 1-halo-4-undecyne compound (6). By using said amount, a preferable reactivity may be ensured.

The reaction temperature of the catalytic hydrogenation reaction varies, depending on the type of catalyst and/or solvent to be used, and is preferably 0 to 160° C., and more preferably 20 to 100° C. By using said reaction temperature and said more preferred reaction temperature, a preferable geometrical selectivity and a more preferred geometrical selectivity may be ensured.

The reaction time of the catalytic hydrogenation reaction is preferably 0.5 to 100 hours. By using said reaction time, a preferable yield may be ensured.

(ii) Reduction Reaction With Zinc Compound in Alcohol Solvent

The reduction reaction is carried out using a zinc compound in an alcohol solvent.

The alcohol used as the solvent has preferably 1 to 10 carbon atoms, and more preferably 1 to 5 carbon atoms. Examples of the alcohol used as the solvent include linear alcohol compounds such as methanol, ethanol, propanol, butanol, pentanol, hexanol, heptanol, octanol, nonanol, and decanol; secondary alcohols such as 2-propanol and 2-butanol; branched alcohol compounds such as isobutyl alcohol; and cyclic alcohol compounds such as cyclohexanol. The alcohol used as the solvent is preferably alcohol compounds having 1 to 5 carbon atoms such as methanol, ethanol, propanol, butanol, pentanol, and 2-propanol. By using said alcohol compounds having 1 to 5 carbon atoms such as methanol, ethanol, propanol, butanol, pentanol, and 2-propanol, a preferable reactivity may be ensured.

The amount of the alcohol used is preferably 46 to 1,000 g, per mol of the 1-halo-4-undecyne compound (6). By using said amount, a preferable reactivity may be ensured.

The amount of the zinc compound used is preferably 1.0 to 1,000 mol, and more preferably 1.0 to 200 mol, per mol of the 1-halo-4-undecyne compound (6). By using said preferred amount and said more preferred amount, a preferable reactivity and a more preferred reactivity may be ensured.

The reduction reaction may require a long reaction time due to low reactivity of the zinc compound and, therefore, an activator for the zinc compound or an activated zinc compound that has been previously prepared may be used, if necessary.

Examples of the activator include 1,2-dibromoethane, cuprous chloride, cuprous bromide, cuprous iodide, lithium bromide, iodine, and chlorotrimethylsilane.

The activator may be used alone or in combination thereof, if necessary.

The amount of the activator used is preferably 0.01 to 10.0 mol, per mol of the 1-halo-4-undecyne compound (6). By using said amount, a preferable reactivity may be ensured.

An activated zinc compound may be prepared, for example, by treating metallic zinc with an acid such as hydrochloric acid, reducing zinc chloride with metallic lithium in tetrahydrofuran or 2-methyltetrahydrofuran, or reacting metallic zinc with 1,2-dibromoethane and lithium dibromocuprate in tetrahydrofuran or 2-methyltetrahydrofuran.

The reaction temperature of the reduction reaction varies, depending on the solvent to be used, and is preferably 20 to 180° C. By using said reaction temperature, a preferable reactivity may be ensured.

The reaction time of the reduction reaction is preferably 0.5 to 150 hours. By using said reaction time, a preferable completion of the reaction may be ensured.

(iii) Hydroboration With Dialkylborane, Followed by Reduction Reaction by Protonation In the reduction reaction, first, hydroboration is carried out with dialkylborane in a solvent.

The dialkylborane used in the hydroboration is preferably 4 to 18 carbon atoms, and more preferably 6 to 12 carbon atoms.

Examples of the dialkylborane include dicyclohexylborane, diisoamylborane, disiamylborane, 9-borabicyclo [3.3.1]nonane (9-BBN), diisopinocampheylborane, catecholborane, and pinacolborane. The dialkylborane is preferably dicyclohexylborane and diisoamylborane. By using said dicyclohexylborane and diisoamylborane, a preferable reactivity may be ensured.

The amount of the dialkylborane used is preferably 1.0 to 4.0 mol, per mol of the 1-halo-4-undecyne compound (6). By using said amount, a preferable reactivity may be ensured.

Examples of the solvent used in the hydroboration include ether solvents such as tetrahydrofuran (THF), 2-methyltetrahydrofuran (2-MeTHF), diethyl ether, dibutyl ether, 4-methyltetrahydropyran, cyclopentylmethylether, 1,4-dioxane, and diethyleneglycol dimethyl ether; and hydrocarbon solvents such as hexane, heptane, benzene, toluene, xylene, and cumene. Ethers such as tetrahydrofuran, 2-methyltetrahydrofuran, 4-methyltetrahydropyran, and diethyleneglycol dimethyl ether are preferred. By using said ethers such as tetrahydrofuran, 2-methyltetrahydrofuran, 4-methyltetrahydropyran, and diethyleneglycol dimethyl ether, a preferable reactivity may be ensured.

The solvent may be used alone or in combination thereof, if necessary. The solvent may be a commercially available one.

The amount of the solvent used is preferably 100 to 3,000 g, per mol of the 1-halo-4-undecyne compound (6). By using said amount, a preferable reactivity may be ensured.

The reaction temperature of the hydroboration is preferably −20° C. to 50° C. By using said reaction temperature, a preferable geometrical selectivity may be ensured.

The reaction time of the hydroboration varies, depending on the reaction temperature and/or the production scale to be used, and is preferably 0.5 to 100 hours. By using said reaction time, a preferable reactivity may be ensured.

In the aforesaid reduction reaction, the protonation is carried out with an acid in a solvent after the hydroboration.

Examples of the acid used in the protonation after the hydroboration include carboxylic acids such as acetic acid, propionic acid, butyric acid, pentanoic acid, pivalic acid, heptanoic acid, trifluoroacetic acid, chloroacetic acid, formic acid, and oxalic acid; sulfonic acids such as p-toluenesulfonic acid; and mineral acids such as sulfuric acid, hydrochloric acid, nitric acid, and phosphoric acid. Carboxylic acids such as acetic acid and propionic acid are preferred. By using said carboxylic acids such as acetic acid and propionic acid, a preferable reactivity may be ensured.

The amount of the acid used is preferably 2.0 to 20.0 mol, per mol of the 1-halo-4-undecyne compound (6). By using said amount, a preferable reactivity may be ensured.

Because the protonation may be carried out in the same reaction system after the hydroboration, the solvent and its amount used in the protonation may be the same as in the hydroboration.

The reaction temperature of the protonation varies, depending on the reagent to be used, and is preferably 0° C. to 150° C. By using said reaction temperature, a preferable reaction rate may be ensured.

The reaction time of the protonation varies, depending on the reaction temperature and/or the production scale to be used, and is preferably 0.5 to 70 hours. By using said reaction time, a preferable reactivity may be ensured.

(iv) Reduction Reaction With Potassium Hydroxide and N,N-dimethylfoiiiiamide (DMF) in the Presence of Palladium Catalyst Such as Palladium Acetate The reduction reaction is carried out with potassium hydroxide and N,N-dimethylformamide (DMF) in the presence of a palladium catalyst such as palladium acetate, preferably at 100 to 180° C. for 0.5 to 100 hours.

(v) Reduction Reaction by Hydrosilylation to Obtain Vinylsilane, Followed by Desilylation The hydrosilylation is carried out with trialkylsilane and metal catalysts such as a Wilkinson catalyst and a Trost catalyst.

The amount of the metal catalyst used is preferably 0.0001 to 4.0 mol, and more preferably 0.001 to 1.0 mol, per mol of the 1-halo-4-undecyne compound (6). By using said preferred amount and said more preferred amount, a preferable reactivity and a more preferred reactivity may be ensured.

The hydrosilylation is preferably carried out at 5 to 100° C. for 0.5 to 100 hours.

The desilylation after the hydrosilylation is preferably carried out with at least one of acids such as sulfuric acid and hydrochloric acid, hydrogen iodide, acetyl chloride, titanium tetrachloride, and iodine at 5° C. to 80° C. for 0.5 to 100 hours.

Thus, the (Z)-1-halo-4-undecene compound (1) can be prepared.

A process for preparing (Z)-7-tetradecen-2-one of the following formula (5) from the aforesaid (Z)-1-halo-4-undecene compound (1) will be explained below in Section D and Section E. (Z)-7-Tetradecen-2-one (5) may be prepared, for example, according to the following chemical reaction formula.

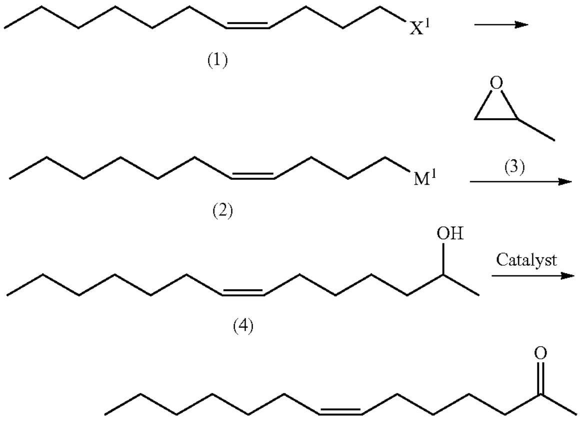

(1) (2) (4) (5)

First, the (Z)-1-halo-4-undecene compound (1) is converted into the nucleophilic reagent, (Z)-4-undecenyl compound (2). The nucleophilic reagent, (Z)-4-undecenyl compound (2), is then subjected to an addition reaction with propylene oxide (3) to form (Z)-7-tetradecen-2-ol (4). (Z)-7-Tetradecen-2-one (5) may then be prepared by subjecting (Z)-7-tetradecen-2-ol of the general formula (4) to an oxidation reaction.

A process for preparing (Z)-7-tetradecen-2-ol (4) will be explained below in Section D.

D. Process for Preparing (Z)-7-tetradecen-2-ol (4) by Converting (Z)-1-halo-4-undecene Compound (1) Into Nucleophilic Reagent, (Z)-4-undecenyl compound (2), and Then Subjecting Nucleophilic Reagent, (Z)-4-undecenyl Compound (2), to Addition Reaction With Propylene Oxide (3)

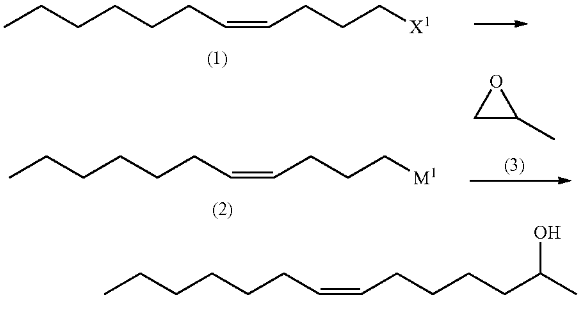

(1) (2) (4)

D-1. Nucleophilic Reagent, (Z)-4-undecenyl Compound (2)

In the general formula (2), $M^1$ represents Li or $MgZ^1$, and $Z^1$ represents a halogen atom or a hexyl group.

Specifically, examples of the halogen atom include a chlorine atom, a bromine atom, and an iodine atom. A chlorine atom and a bromine atom are preferred, and a chlorine atom is particularly preferred. By using said chlorine atom and bromine atom, a preferable availability may be ensured. By using said chlorine atom, particularly preferred availability may be ensured.

The nucleophilic reagent, (2)-4-undecenyl compound (2), may be prepared according to a conventional method or a process described below.

A process for preparing the nucleophilic reagent, (Z)-4-undecenyl compound (2), for example, a (Z)-4-undecenylmagnesium halide reagent (2: $M^1$=$MgZ^1$), will be described below as an example. The (Z)-4-undecenylmagnesium halide reagent (2: $M^1$=$MgZ^1$) may be prepared, for example, by reacting the (Z)-1-halo-4-undecene compound (1) with magnesium in a solvent, as shown in the following chemical reaction formula.

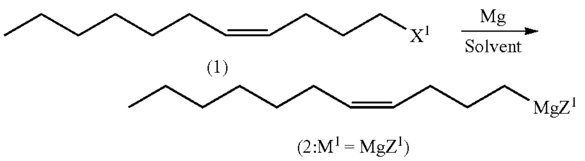

(1)

(2:$M^1$ = $MgZ^1$)

The (Z)-4-undecenylmagnesium halide reagent (2: $M^1$=$MgZ^1$) is a Grignard reagent, wherein $Z^1$ represents a halogen atom or a hexyl group, $Z^1$ is the same as $X^1$ when a halogen atom, and the type of the halogen atom does not change before and after the reaction.

The (Z)-1-halo-4-undecene compound (1) may be used alone or in combination thereof. The (Z)-1-halo-4-undecene compound (1) may be a commercially available one or may be synthesized in house.

The amount of magnesium used is preferably 1.0 to 2.0 gram atoms, per mol of the (Z)-1-halo-4-undecene compound (1). By using said amount, a preferable completion of the reaction may be ensured.

Examples of the solvent include ether solvents such as tetrahydrofuran (THF), 2-methyltetrahydrofuran (2-MeTHF), diethyl ether, dibutyl ether, 4-methyltetrahydropyran (MTHP), cyclopentylmethylether, and 1,4-dioxane; hydrocarbon solvents such as hexane, heptane, benzene, toluene, xylene, and cumene; and polar solvents such as N,N-dimethylformamide (DMF), N,N-dimethylacetamide (DMAC), N-methylpyrrolidone (NMP), dimethyl sulfoxide (DMSO), γ-butyrolactone (GBL), acetonitrile, N,N'-dimethylpropylene urea (DMPU), hexamethylphosphoric triamide (HMPA), dichloromethane, and chloroform. The solvent is preferably ether solvents such as tetrahydrofuran, 2-methyltetrahydrofuran, diethyl ether, and 4-methyltetrahydropyran, and more preferably tetrahydrofuran and 2-methyltetrahydrofuran. By using said ether solvents such as tetrahydrofuran, 2-methyltetrahydrofuran, diethyl ether, and 4-methyltetrahydropyran, a preferable reaction rate of the Grignard reagent formation may be ensured. By using said tetrahydrofuran and 2-methyltetrahydrofuran, a more preferred reaction rate of the Grignard reagent formation may be ensured.

The solvent may be used alone or in combination thereof, if necessary. The solvent may be a commercially available one.

The amount of the solvent used is preferably 30 to 5,000 g, and more preferably 50 to 3,000 g, per mol of the (Z)-1-halo-4-undecene compound (1). By using said preferred amount and said more preferred amount, a preferable reactivity and a more preferred reactivity may be ensured.

The reaction temperature of the aforesaid reaction with magnesium varies, depending on the solvent to be used, and is preferably 30 to 120° C. By using said reaction temperature, a preferable reactivity may be ensured.

The reaction time of the aforesaid reaction with magnesium varies, depending on the solvent and/or the production scale to be used, and is preferably 0.5 to 100 hours. By using said reaction time, a preferable reactivity may be ensured.

D-2. Process for Preparing (Z)-7-tetradecen-2-ol (4) by Subjecting (Z)-4-undecenylmagnesium Halide Reagent (2: $M^1$=$MgZ^1$) to Addition Reaction With Propylene Oxide (3)

The amount of propylene oxide (3) used is preferably 1.0 to 10.0 mol, and more preferably 1.0 to 5.0 mol, per mol of the (Z)-1-halo-4-undecene compound (1). By using said preferred amount and said more preferred amount, a preferable reactivity and a more preferred reactivity may be ensured.

A catalyst may be incorporated in the addition reaction mentioned above, if necessary.

Examples of the catalyst include copper compounds such as cuprous halides such as cuprous chloride, cuprous bromide, and cuprous iodide and cupric halides such as cupric chloride, cupric bromide, and cupric iodide; iron compounds such as iron(II) chloride, iron(III) chloride, iron(II) bromide, iron(III) bromide, iron(II) iodide, iron(III) iodide, and iron (III) acetylacetonate; silver compounds such as silver chloride, silver nitrate, and silver acetate; titanium compounds such as titanium tetrachloride, titanium tetrabromide, titanium(IV) methoxide, titanium(IV) ethoxide, titanium(IV) isopropoxide, and titanium(IV) oxide; palladium(II) compounds such as dichlorobis(triphenylphosphine)palladium and dichloro[1,1'-bis(diphenylphosphino)ferrocene]palladium; and nickel compounds such as nickel chloride, dichloro[1,2-bis(diphenylphosphino)ethane]nickel(II), and dichlorobis(triphenylphosphine)nickel(II). The catalyst is preferably copper compounds, and more preferably cuprous halides such as cuprous chloride, cuprous bromide, and cuprous iodide. By using said copper compounds, a preferable reactivity and/or economy may be ensured. By using said cuprous halides such as cuprous chloride, cuprous bromide, and cuprous iodide, a more preferred reactivity and/or economy may be ensured.

The catalyst may be used alone or in combination thereof, if necessary. The catalyst may be a commercially available one.

The amount of the catalyst used is preferably 0.00001 to 1.00 mol, and more preferably 0.0001 to 0.300 mol, per mol of the (Z)-1-halo-4-undecene compound (1). By using said preferred amount and said more preferred amount, a preferable reaction rate and post-processing and a more preferred reaction rate and post-processing may be ensured.

A solvent may be incorporated in the addition reaction mentioned above, if necessary. Examples of the solvent include general solvents such as, for example, ether solvents such as tetrahydrofuran (THF), 2-methyltetrahydrofuran (2-MeTHF), diethyl ether, dibutyl ether, 4-methyltetrahydropyran (MTHP), cyclopentylmethylether, and 1,4-dioxane; hydrocarbon solvents such as hexane, heptane, benzene, toluene, xylene, and cumene; and polar solvents such as N,N-dimethylformamide (DMF), N,N-dimethylacetamide (DMAC), N-methylpyrrolidone (NMP), dimethyl sulfoxide (DMSO), γ-butyrolactone (GBL), acetonitrile, N,N'-dimethylpropylene urea (DMPU), hexamethylphosphoric triamide (HMPA), dichloromethane, and chloroform. The solvent is preferably ether solvents such as diethyl ether, tetrahydrofuran, 2-methyltetrahydrofuran, and 4-methyltetrahydropyran; and hydrocarbon solvents such as toluene and xylene. By using said ether solvents such as diethyl ether, tetrahydrofuran, 2-methyltetrahydrofuran, and 4-methyltetrahydropyran; and hydrocarbon solvents such as toluene and xylene, a preferable reactivity may be ensured.

The solvent may be used alone or in combination thereof, if necessary. The solvent may be a commercially available one.

The amount of the solvent used is preferably 20 to 7,000 g, and more preferably 50 to 3,000 g, per mol of the (Z)-1-halo-4-undecene compound (1). By using said preferred amount and said more preferred amount, a preferable reactivity and a more preferred reactivity may be ensured.

The reaction temperature of the addition reaction varies, depending on the (Z)-4-undecenylmagnesium halide reagent (2: $M^1$=$MgZ^1$) and/or the solvent to be used, and is preferably −40 to 180° C., more preferably −25 to 100° C., and most preferably −10 to 70° C. By using said preferred reaction temperature, said more preferred reaction temperature, and said most preferred reaction temperature, a preferable reactivity, a more preferred reactivity, and a most preferred reactivity may be ensured.

The reaction time of the addition reaction varies, depending on the nucleophilic reagent, the solvent, and/or the production scale to be used, and is preferably 0.5 to 100 hours. By using said reaction time, a preferable reactivity may be ensured.

A process for preparing (Z)-7-tetradecen-2-one (5) will be explained below in Section E.

E. Process for Preparing (Z)-7-tetradecen-2-one (5) by Subjecting (Z)-7-tetradecen-2-ol (4) to Oxidation Reaction

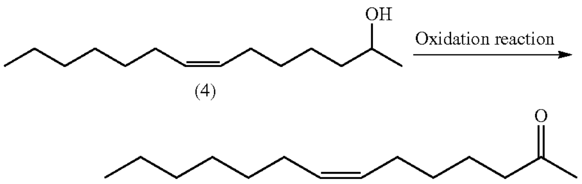

(4)

(5)

Oxidation Reaction

The oxidation reaction may be carried out, for example, by a Corey-Kim oxidation carried out with N-chlorosuccinimide, dimethyl sulfide, and triethylamine, a Swern oxidation carried out with dimethyl sulfoxide and oxalyl chloride in a solvent, followed by triethylamine, a TEMPO oxidization carried out with sodium hypochlorite using a catalyst such as 2,2,6,6-tetramethylpiperidine 1-oxyl (TEMPO) and 2-hydroxy-2-azaadamantane, a Jones oxidation carried out with chromium trioxide and sulfuric acid, a chromic acid oxidation carried out with chromic acid, a Dess-Martin oxidation using Dess-Martin periodinane as an oxidizing agent, a Ley-Griffith oxidation (TPAP oxidization) with tetrapropylammonium perruthenate as an oxidation catalyst and 4-methylmorpholine N-oxide as a re-oxidizing agent of ruthenium, an Oppenauer oxidation carried out using a hydrogen acceptor with an aluminum compound or a magnesium compound as a catalyst, or modifications thereof. Among these oxidation reactions, the Oppenauer oxidation and its modifications are particularly preferred due to their low environmental toxicity and low risk of explosion. An Oppenauer oxidation refers to a reaction using an aluminum compound, and particularly aluminum triisopropoxide. Modifications of the Oppenauer oxidation refer to reactions using a compound other than an aluminum compound such as, for example, a magnesium compound. Other modifications of the Oppenauer oxidation may use a mixture of an aluminum compound and the aforesaid compound other than an aluminum compound.

A preparation process using the Oppenauer oxidation reaction and its modifications as the oxidation reaction will be described below as an example. The Oppenauer oxidation reaction and its modifications may be carried out, for example, as shown in the following chemical reaction formula in which the aforesaid (Z)-7-tetradecen-2-ol (4) is oxidized in the presence of a hydrogen acceptor with an aluminum compound and a magnesium compound as catalysts, and in a solvent, if necessary.

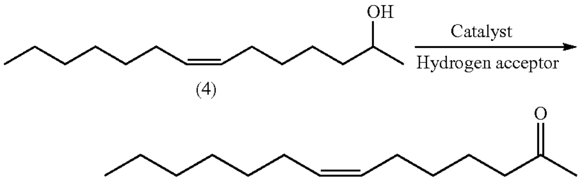

(4)

(5)

Examples of the aluminum compound include trialkylaluminum compounds such as trimethylaluminum and triethylaluminum; and aluminum trialkoxide compounds such as aluminum triisopropoxide and aluminum tri tert-butoxide.

Examples of the magnesium compound include magnesium halide compounds such as magnesium chloride and magnesium bromide; magnesium hydroxide; and magnesium alkoxide compounds such as magnesium methoxide, magnesium ethoxide, and magnesium tert-butoxide.

The catalyst may be used alone or in combination thereof, if necessary. The catalyst may be a commercially available one.

The amount of the catalyst used is preferably 0.1 to 5.0 mol, and more preferably 0.5 to 3.0 mol, per mol of (Z)-7-tetradecen-2-ol (4). By using said preferred amount and said more preferred amount, a preferable reactivity and a more preferred reactivity may be ensured.

Examples of the hydrogen acceptor include ketone compounds such as acetone, ethyl methyl ketone, diethyl ketone, ethyl propyl ketone, isobutyl methyl ketone, diisobutyl ketone, and cyclohexanone; and aldehyde compounds such as pivaldehyde, benzaldehyde, and cyclohexanecarboxyaldehyde.

The hydrogen acceptor may be used alone or in combination thereof, if necessary. The hydrogen acceptor may be a commercially available one.

The amount of the hydrogen acceptor used is preferably 1.0 to 10,000 mol, and more preferably 1.0 to 500 mol, per mol of (Z)-7-tetradecen-2-ol (4). By using said preferred amount and said more preferred amount, a preferable reactivity and a more preferred reactivity may be ensured.

A solvent may be incorporated in the Oppenauer oxidation reaction, if necessary. Examples of the solvent include ether solvents such as tetrahydrofuran (THF), 2-methyltetrahydrofuran (2-MeTHF), diethyl ether, dibutyl ether, 4-methyltetrahydropyran (MTHP), cyclopentylmethylether, and 1,4-dioxane; hydrocarbon solvents such as hexane, heptane, benzene, toluene, xylene, and cumene; polar solvents such as N,N-dimethylformamide (DMF), N,N-dimethylacetamide (DMAC), N-methylpyrrolidone (NMP), dimethyl sulfoxide (DMSO), γ-butyrolactone (GBL), acetonitrile, acetone, N,N'-dimethylpropylene urea (DMPU), hexamethylphosphoric triamide (HMPA), dichloromethane, chloroform, and acetone; and ester solvents such as methyl acetate, ethyl acetate, n-propyl acetate, and n-butyl acetate. The solvent is preferably ether solvents such as 4-methyltetrahydropyran; and hydrocarbon solvents such as toluene and xylene. By using said ether solvents such as 4-methyltetrahydropyran; and hydrocarbon solvents such as toluene and xylene, a preferable reactivity may be ensured.

The solvent may be used alone or in combination thereof, if necessary. The solvent may be a commercially available one.

The amount of the solvent used in the Oppenauer oxidation reaction is preferably 0 to 9,000 g, and more preferably 100 to 5,000 g, per mol of (Z)-7-tetradecen-2-ol (4).

The reaction temperature of the Oppenauer oxidation reaction varies, depending on the catalyst and/or the solvent to be used, and is preferably 5 to 180° C., and more preferably 50 to 140° C. By using said preferred reaction temperature and said more preferred reaction temperature, a preferable reactivity and a more preferred reactivity may be ensured.

The reaction time of the halogenation reaction varies, depending on the production scale to be used, and is preferably 0.5 to 100 hours. By using said reaction time, a preferable reactivity may be ensured.

In the Oppenauer oxidation reaction, the by-product alcohol compounds are evaporated off, and the addition of the hydrogen acceptor increases the conversion percentage, thereby allowing an increase of ease of preparation by reducing the reaction time and/or increasing the quantity of starting materials. When using aluminum triisopropoxide as a catalyst and acetone as a hydrogen acceptor, for example, (Z)-7-tetradecen-2-ol (4), aluminum triisopropoxide, acetone, and the solvent are combined together and then heated, followed by evaporating the isopropyl alcohol by-product and adding a certain amount of acetone. The Oppenauer oxidation reaction may be carried out efficiently by repeating this procedure.

The preparation of (Z)-7-tetradecen-2-one (5) in which the Oppenauer oxidation reaction is used to oxidize the hydroxy group of (Z)-7-tetradecen-2-ol (4) is an equilibrium reaction, which may result in an incomplete reaction. The equilibrium may be biased in such a case, for example, by using a large excess of acetone and/or separating the unreacted (Z)-7-tetradecen-2-ol (4). However, it is preferred to separate the unreacted (Z)-7-tetradecen-2-ol (4) because the use of a large excess of acetone results in a drastic reduction of the quantity of starting materials and the ease of preparation.

(Z)-7-Tetradecen-2-ol (4) and (Z)-7-tetradecen-2-one (5) have boiling points near each other, making it difficult to separate by distillation. For this reason, examples of processes for separating the unreacted (Z)-7-tetradecen-2-ol (4) include separation by silica gel column chromatography; and/or distillation to separate (Z)-7-tetradecen-2-one (5) and esterified compounds of (Z)-7-tetradecen-2-ol (4) by utilizing the boiling point difference between the two, after esterifying the unreacted (2)-7-tetradecen-2-ol (4) to form the esterified compounds of (Z)-7-tetradecen-2-ol (4) so that the boiling points of the esterified compounds are higher than the boiling point of (Z)-7-tetradecen-2-ol (4).

Silica gel column chromatography separates (Z)-7-tetradecen-2-ol (4) and (Z)-7-tetradecen-2-one (5) by utilizing the different polarities of the two compounds. Silica gel column chromatography may be carried out by conventional methods, but is difficult to use for larger scales considering, for example, cost and/or production efficiency.

The process of esterifying the unreacted (Z)-7-tetradecen-2-ol (4) to form esterified compounds of (Z)-7-tetradecen-2-ol (4) having higher boiling points than (Z)-7-tetradecen-2-ol (4), followed by distilling to separate (Z)-7-tetradecen-2-one (5) and the esterified compounds of (Z)-7-tetradecen-2-ol (4), is applicable even for large scales, and is therefore preferred over the separation by the aforesaid silica gel column chromatography.

The esterification may be carried out, for example, by adding an esterifier to the reaction mixture after the Oppenauer oxidation reaction or to a concentrated solution after evaporating the solvent from the reaction mixture.

Examples of the esterifier used in the esterification reaction include acid anhydrides such as acetic anhydride, propionic anhydride, butanoic anhydride, pivalic anhydride, and benzoic anhydride; and acid chlorides such as acetyl chloride, propionyl chloride, butyryl chloride, pivaloyl chloride, and benzoyl chloride. The esterifier is preferably acid anhydrides such as butanoic anhydride, pivalic anhydride, and benzoic anhydride; and acid chlorides such as butyryl chloride, pivaloyl chloride, and benzoyl chloride. By using said acid anhydrides such as butanoic anhydride, pivalic anhydride, and benzoic anhydride; and acid chlorides such as butyryl chloride, pivalic chloride, and benzoyl chloride, a preferable boiling point difference may be ensured.

The amount of the esterifier used is preferably 1.0 to 10.0 mol, and more preferably 1.0 to 5.0 mol, per mol of the remaining unreacted (Z)-7-tetradecen-2-ol (4). By using said preferred amount and said more preferred amount, a preferable reactivity and economy and a more preferred reactivity and economy may be ensured. The amount of the unreacted (Z)-7-tetradecen-2-ol (4) can be measured, for example, by GC analysis. Specifically, for example, post-processing and concentration are carried out after the Oppenauer oxidation to obtain the reaction mixture of (Z)-7-tetradecen-2-one (5) and (Z)-7-tetradecen-2-ol (4), and the weight of the reaction mixture is measured. The GC % from the GC analysis of the reaction mixture may be multiplied by the weight of the reaction mixture to calculate the amounts of (Z)-7-tetradecen-2-one (5) and (Z)-7-tetradecen-2-ol (4).

An acid or a base may be incorporated in the esterification, if necessary.

Examples of the acid include mineral acids such as hydrochloric acid, sulfuric acid, and nitric acid; aromatic sulfonic acids such as benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, magnesium chloride, magnesium bromide, titanium tetrachloride, titanium tetrabromide, titanium(IV) methoxide, titanium(IV) ethoxide, titanium (IV) isopropoxide, and titanium(IV) oxide.

The acid may be used alone or in combination thereof, if necessary.

The amount of the acid used is preferably 0.001 to 3.00 mol, and more preferably 0.01 to 1.50 mol, per mol of the remaining unreacted (Z)-7-tetradecen-2-ol (4). By using said preferred amount and said more preferred amount, a preferable reactivity and economy and a more preferred reactivity and economy may be ensured.

Examples of the base include trialkylamine compounds such as trimethylamine, triethylamine, and N,N-diisopropylethylamine; cyclic amine compounds such as piperidine, pyrrolidine, and 1,8-diazabicyclo[5.4.0]-7-undecene (DBU); aromatic amine compounds such as pyridine, lutidine, N,N-dimethylaniline, N,N-diethylaniline, N,N-dibutylaniline, and 4-dimethylaminopyridine; and metal alkoxides such as sodium methoxide, sodium ethoxide, sodium tert-butoxide, sodium tert-amyloxide, lithium methoxide, lithium ethoxide, lithium tert-butoxide, lithium tert-amyloxide, potassium methoxide, potassium ethoxide, potassium tert-butoxide, and potassium tert-amyloxide.

The base may be used alone or in combination thereof, if necessary.

The amount of the base used is preferably 0.010 to 10.0 mol, and more preferably 0.001 to 5.0 mol, per mol of the remaining (Z)-7-tetradecen-2-ol (4). By using said preferred amount and said more preferred amount, a preferable reactivity and economy and a more preferred reactivity and economy may be ensured.

A solvent may be incorporated in the esterification, if necessary.

Examples of the solvent include general solvents such as, for example, ether solvents such as tetrahydrofuran (THF), 2-methyltetrahydrofuran (2-MeTHF), diethyl ether, dibutyl ether, 4-methyltetrahydropyran (MTHP), cyclopentylmethylether, and 1,4-dioxane; hydrocarbon solvents such as hexane, heptane, benzene, toluene, xylene, and cumene; and polar solvents such as N,N-dimethylformamide (DMF), N,N-dimethylacetamide (DMAC), N-methylpyrrolidone (NMP), dimethyl sulfoxide (DMSO), γ-butyrolactone (GBL), acetonitrile, N,N'-dimethylpropylene urea (DMPU), hexamethylphosphoric triamide (HMPA), dichloromethane, and chloroform. The solvent is preferably ether solvents such as diethyl ether, tetrahydrofuran, 2-methyltetrahydrofuran, and 4-methyltetrahydropyran; and hydrocarbon solvents such as toluene and xylene. By using said ether solvents such as diethyl ether, tetrahydrofuran, 2-methyltetrahydrofuran, and 4-methyltetrahydropyran; and hydrocarbon solvents such as toluene and xylene, a preferable reactivity may be ensured.

The solvent may be used alone or in combination thereof, if necessary. The solvent may be a commercially available one.

A solvent may be incorporated in the acetylation, if necessary.

The amount of the solvent used in the acetylation is preferably 0 to 8,000 g, and more preferably 0 to 5,000 g, per mol of the aforesaid remaining (Z)-7-tetradecen-2-ol (4).

The reaction temperature of the esterification varies, depending on the esterifier and/or the solvent to be used, and is preferably −40 to 140° C., more preferably 0 to 100° C., and most preferably 20 to 80° C. By using said preferred reaction temperature, said more preferred reaction temperature, and said most preferred reaction temperature, a preferable reactivity, a more preferred reactivity, and a most preferred reactivity may be ensured.

The reaction time of the esterification is preferably 0.5 to 100 hours. By using said reaction time, a preferable reactivity may be ensured.

Thus, (Z)-7-tetradecen-2-one (5) may be separated by distillation by esterifying the remaining unreacted (Z)-7-tetradecen-2-ol (4) to form a boiling point difference between (Z)-7-tetradecen-2-one (5) and the esterified compounds of (Z)-7-tetradecen-2-ol (4) obtained by the esterification. The esterified compounds that are separated may be recycled as starting materials of a subsequent reaction batch, for example, by being returned to (Z)-7-tetradecen-2-ol (4) by a hydrolysis reaction.

Thus, (Z)-7-tetradecen-2-one (5), the sex pheromone of the Oriental beetle, can be efficiently prepared with fewer steps from the synthetic intermediate, (Z)-1-halo-4-undecene compound (1). The process for preparing is suited to an industrial scale.

EXAMPLES

The present invention will be described with reference to the following Examples. It should be noted that the present invention is not limited to or by the Examples.

The term “purity” as used herein means an area percentage in gas chromatography (GC), unless otherwise specified. The term “product ratio” means a ratio of area percentages in GC. The term “yield” is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-5 or DB-WAX, 0.25 μm×0.25 mmϕ×30 m; carrier gas: He (1.55 mL/min), detector: FID; column temperature: 150° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]×100

THF represents tetrahydrofuran, EDA represents ethylenediamine, Et represents an ethyl group, and $^{i}$Pr represents an isopropyl group.

Example 1: Preparation of 1-chloro-4-undecyne (6: $X^1$=Cl)

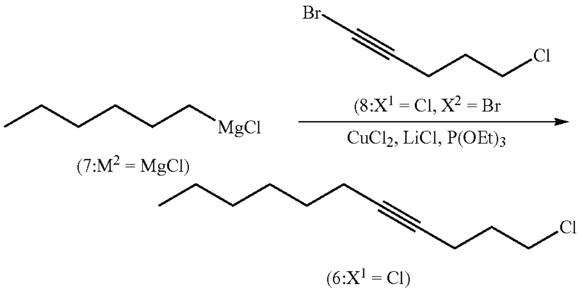

(7:$M^2$ = MgCl)

(6:$X^1$ = Cl)

Cupric chloride ($CuCl_2$) (19.20 g, 0.144 mol), triethyl phosphite ($P(OEt)_3$) (95.52 g, 0.56 mol), lithium chloride (LiCl) (12.12 g, 0.28 mol), tetrahydrofuran (1,635.68 g), and a xylene solution of 1-bromo-5-chloro-1-pentyne (8: $X^1$=Cl and $X^2$=Br) (5,341.08 g, purity 37.1%, 10.92 mol of 1-bromo-5-chloro-1-pentyne) were placed in a reactor at a room temperature, and then a tetrahydrofuran solution of hexylmagnesium chloride (7: $M^2$=MgCl) (5,365.64 g, 12.00 mol of hexylmagnesium chloride) was added dropwise at 20 to 35° C. After the completion of the dropwise addition, the mixture was stirred at 25 to 35° C. for 3 hours. An aqueous solution of acetic acid (prepared from acetic acid (1,174.04 g) and water (3,522.16 g)) was then added to the reaction mixture, followed by phase separation. The aqueous layer was removed to obtain the organic layer. The organic layer thus obtained was concentrated at a reduced pressure, and the resulting concentrate was distilled at a reduced pressure to obtain 1-chloro-4-undecyne (6: $X^1$=Cl) (1,668.32 g, 8.67 mol, purity 97.08%, b.p.=99.0 to 101.3° C./0.4 kPa (3.0 mmHg)) with a yield of 72.28%.

The following is the spectrum data of 1-chloro-4-undecyne (6: $X^1$=Cl) thus obtained.

Nuclear magnetic resonance spectrum: $^{1}$H-NMR (500 MHz, $CDCl_3$): δ=0.88 (3H, t, J=7.3 Hz), 1.22-1.40 (6H, m), 1.47 (2H, q-like, J=7.3 Hz), 1.92 (2H, tt, J=6.9 Hz, 6.9 Hz), 2.13 (2H, tt, J=7.3 Hz, 2.3 Hz), 2.33 (2H, tt, J=6.9 Hz, 2.3 Hz), 3.65 (2H, t, J=6.5 Hz); $^{13}$C-NMR (500 MHz, $CDCl_3$): δ=14.02, 16.19, 18.68, 22.55, 28.52, 28.98, 31.33, 31.79, 43.78, 77.96, 81.44.

Mass spectrum: EI-mass spectrum (70 eV): m/z 185 ($M^+$−1), 123, 109, 95, 81, 67, 53.

Infrared absorption spectrum: (D-ATR): νmax=2957, 2931, 2858, 1456, 1435, 1290, 727, 654 $cm^{-1}$.

Example 2: Preparation of (Z)-1-halo-4-undecene (1: $X^1$=Cl)

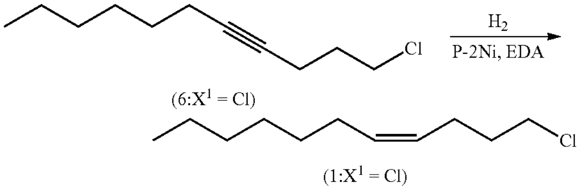

(6:$X^1$ = Cl)

(1:$X^1$ = Cl)

1-Chloro-4-undecyne (6: $X^1$=Cl) (1,414.25 g, 7.35 mol, purity 97.08%) obtained in Example 1, P-2 Ni catalyst (460.60 g, 0.12 mol of Ni), and ethylenediamine (EDA) (10.04 g) were placed in a reactor at a room temperature, and then hydrogen was added while stirring at 45 to 55° C. for 9.5 hours. After the conversion was confirmed to be 100% by GC, water (321.49 g) was added to the reaction mixture, followed by phase separation. The aqueous layer was removed to obtain the organic layer. The organic layer thus obtained was concentrated at a reduced pressure, and the resulting concentrate was distilled at a reduced pressure to obtain (Z)-1-halo-4-undecene (1: $X^1$=Cl) (1,385.23 g, 6.96 mol, purity 94.79%, b.p.=92.1 to 95.0° C./0.40 kPa (3.0 mmHg)) with a yield of 94.62%.

The following is the spectrum data of (Z)-1-halo-4-undecene (1: $X^1$=Cl) thus obtained.

Nuclear magnetic resonance spectrum: $^{1}$H-NMR (500 MHz, $CDCl_3$): δ=0.89 (3H, t, J=7.3 Hz), 1.23-1.38 (8H, m), 1.82 (2H, tt, J=6.9 Hz, 6.9 Hz), 2.04 (2H, q-like, J=6.5 Hz), 2.20 (2H, q-like, J=7.3 Hz), 3.54 (2H, t, J=6.5 Hz), 5.27-5.34 (1H, m), 5.40-5.47 (1H, m); $^{13}$C-NMR (500 MHz, $CDCl_3$): δ=14.09, 22.64, 24.37, 27.23, 28.97, 29.65, 31.75, 32.49, 44.50, 127.49, 131.71.

Mass spectrum: EI-mass spectrum (70 eV): m/z 188 ($M^+$), 123, 109, 97, 81, 69, 55, 41.

Infrared absorption spectrum: (D-ATR): νmax=2956, 2926, 2855, 1457, 727, 655 $cm^{-1}$.

Example 3: Preparation of (Z)-7-tetradecen-2-ol (4)

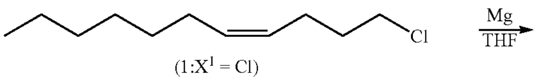

(1:$X^1$ = Cl)

-continued

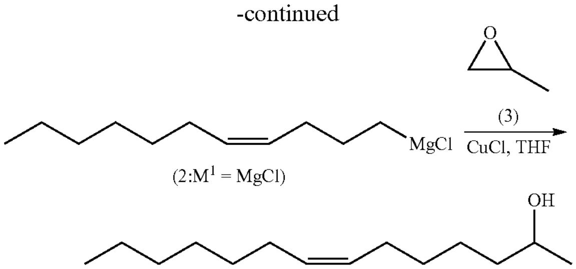

(2:M[1] = MgCl)

(4)

Magnesium (51.26 g, 2.11 mol) and tetrahydrofuran (602.70 g) were placed in a reactor at a room temperature and stirred at 60 to 65° C. for 19 minutes. After the completion of the stirring, (Z)-1-halo-4-undecene (1: $X^1$=Cl) (400.00 g, 2.009 mol, purity 94.79%) prepared in Example 2 was added dropwise to the reactor at 60 to 75° C. After the completion of the dropwise addition, the mixture was stirred at 75 to 80° C. for 4 hours to form (Z)-4-undecenylmagnesium chloride (2: $M^1$=MgCl).

Subsequently, cuprous chloride (CuCl) (0.42 g, purity 95%, 0.004 mol) was added to the reactor at 0 to 10° C., and then propylene oxide (3) (134.19 g, 2.31 mol) was added dropwise at 0 to 30° C. After the completion of the dropwise addition, the reaction mixture was stirred at 20 to 30° C. for 2 hours. Subsequently, an aqueous solution of acetic acid (prepared from acetic acid (251.10 g) and water (753.35 g)) and hexane (178.58 g) were added to the reaction mixture, followed by phase separation. The aqueous layer was removed to obtain the organic layer. The organic layer thus obtained was concentrated at a reduced pressure, and the resulting concentrate was distilled at a reduced pressure to obtain (Z)-7-tetradecen-2-ol (4) (371.58 g, 1.67 mol, purity 95.16%, b.p.=120.8 to 124.2° C./0.4 kPa (3.0 mmHg)) with a yield of 82.87%.

The following is the spectrum data of (Z)-7-tetradecen-2-ol (4) thus obtained.

Nuclear magnetic resonance spectrum: $^1$H-NMR (500 MHz, $CDCl_3$): δ=0.88 (3H, t, J=6.9 Hz), 1.18 (3H, J=6.2 Hz), 1.22-1.50 (14H, m), 1.46 (1H, br.s), 1.97-2.07 (4H, m), 3.78 (1H, sext-like, J=6.1 Hz), 5.30-5.39 (2H, m); $^{13}$C-NMR (500 MHz, $CDCl_3$): δ=14.06, 22.62, 23.44, 25.39, 27.12, 27.21, 28.96, 29.69, 29.72, 31.75, 39.23, 68.09, 129.50, 130.14.

Mass spectrum: EI-mass spectrum (70 eV): m/z 212 ($M^+$), 194, 165, 152, 138, 123, 109, 95, 82, 67, 55, 41.

Infrared absorption spectrum: (D-ATR): νmax=3344, 2959, 2926, 2856, 1462, 1376, 1123, 724 $cm^{-1}$.

Example 4: Preparation of (Z)-7-tetradecen-2-one (5)

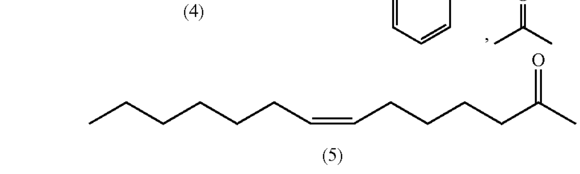

(4)

(5)

(Z)-7-Tetradecen-2-ol (4) (33.48 g, 0.15 mol, purity 95.16%) prepared in Example 3, acetone (100.00 g, 1.72 mol), and toluene (169.37 g) were placed in a reactor at a room temperature and stirred at 75 to 85° C. for 10 minutes. After stirring, a toluene solution of aluminum triisopropoxide was formed by dissolving aluminum triisopropoxide ($Al(O^iPr)_3$) (52.08 g, 0.25 mol) in toluene (254.06 g), and added dropwise to the reactor at 75 to 80° C. After the completion of the dropwise addition, reflux was carried out for 0.5 hours, and a mixture of isopropyl alcohol and acetone was distilled off. The distillation was stopped when the internal temperature reached 87° C., and then acetone (100.00 g, 1.72 mol) was added. After adding acetone, reflux was carried out for 0.5 hours. After the completion of the reflux, a mixture of isopropyl alcohol and acetone was distilled off. The distillation was stopped when the internal temperature reached 87° C., and then acetone (100.00 g, 1.72 mol) was added again. After adding acetone, reflux was carried out for 0.5 hours. After the completion of the reflux, a mixture of isopropyl alcohol and acetone was distilled off. The distillation was stopped when the internal temperature reached 87° C., and then more acetone (100.00 g, 1.72 mol) was added. After adding acetone, reflux was carried out for 0.5 hours. After the completion of the reflux, a mixture of isopropyl alcohol and acetone was distilled off. The distillation was stopped when the internal temperature reached 91° C., followed by cooling to an internal temperature of 30° C. After the cooling, 20% by mass hydrochloric acid (300.00 g with 1.65 mol of hydrogen chloride) and water (200.00 g) were added, followed by phase separation. The aqueous layer was removed, followed by washing with an aqueous solution of sodium bicarbonate (prepared from sodium bicarbonate (4.0 g) and water (300 g)). The aqueous layer was removed to obtain the organic layer. The organic layer thus obtained was concentrated at a reduced pressure, and the resulting concentrate was purified by silica gel column chromatography (hexane:ethyl acetate=40:1 to 2:1) to obtain (Z)-7-tetradecen-2-one (5) (26.30 g, 0.12 mol, purity 93.73%) with a yield of 78.15%, and (Z)-7-tetradecen-2-ol (4) (13.87 g, 0.024 mol, purity 36.18%) of the starting material with a recovery yield of 15.76%.

The following is the spectrum data of (Z)-7-tetradecen-2-one (5) thus obtained.

Nuclear magnetic resonance spectrum: $^1$H-NMR (500 MHz, $CDCl_3$): δ=0.87 (3H, t, J=7.3 Hz), 1.20-1.38 (10H, m), 1.58 (2H, tt, J=7.6 Hz, 7.6 Hz), 1.97-2.05 (4H, m), 2.12 (3H, s), 2.41 (2H, t, J=7.3 Hz), 5.28-5.39 (2H, m); $^{13}$C-NMR (500 MHz, $CDCl_3$): δ=14.06, 22.61, 23.47, 26.91, 27.21, 28.96, 29.22, 29.66, 29.80, 31.74, 43.63, 129.08, 130.40, 209.07.

Mass spectrum: EI-mass spectrum (70 eV): m/z 210 ($M^+$), 192, 167, 152, 139, 125, 111, 97, 84, 71, 55, 43.

Infrared absorption spectrum: (D-ATR): νmax=2927, 2856, 1718, 1458, 1358, 1159, 724 $cm^{-1}$.

Example 5: Preparation of (Z)-7-tetradecen-2-one (5)

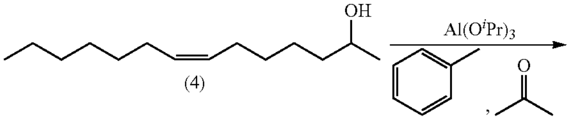

(4)

-continued

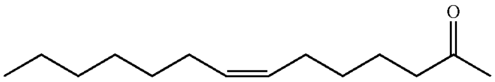

(5)

(Z)-7-Tetradecen-2-ol (4) (44.63 g, 0.20 mol, purity 95.16%) prepared in Example 3, acetone (100.00 g, 1.72 mol), and toluene (100.00 g) were placed in a reactor and stirred at 75 to 85° C. for 10 minutes. After the completion of the stirring, aluminum triisopropoxide (65.36 g, 0.32 mol) was dissolved in toluene (300.00 g) and added dropwise to the reactor at 75 to 80° C.

Reflux was then carried out for 0.5 hours, and then a mixture of isopropyl alcohol and acetone was distilled off The distillation was stopped when the internal temperature reached 87° C., and then acetone (100.00 g, 1.72 mol) was added. After adding acetone, reflux was carried out for 0.5 hours. After the completion of the reflux, a mixture of isopropyl alcohol and acetone was distilled off The distillation was stopped when the internal temperature reached 87° C., and then acetone (100.00 g, 1.72 mol) was added again. After adding acetone, reflux was carried out for 0.5 hours. After the completion of the reflux, a mixture of isopropyl alcohol and acetone was distilled off The distillation was stopped when the internal temperature reached 87° C., and then more acetone (100.00 g, 1.72 mol) was added. After adding acetone, reflux was carried out for 0.5 hours. After the completion of the reflux, a mixture of isopropyl alcohol and acetone was distilled off The distillation was stopped when the internal temperature reached 87° C., and then acetone (100.00 g, 1.72 mol) was added again. After adding acetone, reflux was carried out for 0.5 hours. After the completion of the reflux, a mixture of isopropyl alcohol and acetone was distilled off The distillation was stopped when the internal temperature reached 91° C., followed by cooling to an internal temperature of 30° C. After the cooling, 20% by mass hydrochloric acid (376.00 g with 2.06 mol of hydrogen chloride) and water (251.00 g) were added, followed by phase separation. The aqueous layer was removed, followed by washing with an aqueous solution of sodium bicarbonate (prepared from sodium bicarbonate (4.0 g) and water (300 g)). The aqueous layer was removed to obtain the organic layer. The organic layer thus obtained was concentrated at a reduced pressure, and the resulting concentrate was placed in a new reactor. Pyridine (12.54 g, 0.16 mol) and toluene (100 g) were then added, and then benzoyl chloride (17.82 g, 0.13 mol) was added dropwise at 20 to 30° C.

After the completion of the dropwise addition, stirring was carried out at 45 to 55° C. for 2.5 hours, and it was confirmed by GC that the remaining unreacted (Z)-7-tetradecen-2-ol (4) was subjected to benzoation to form (Z)-7-tetradecen-2-yl benzoate. Water (100.00 g) was added to the reaction mixture including (Z)-7-tetradecen-2-yl benzoate thus formed, followed by phase separation. The aqueous layer was removed to obtain the organic layer. The organic layer thus obtained was concentrated at a reduced pressure, and the resulting concentrate was distilled at a reduced pressure to separately obtain (Z)-7-tetradecen-2-one (5) (37.61 g, 0.15 mol, purity 86.30%, b.p.=101.1 to 120.2° C./0.4 kPa (3.0 mmHg)) with a yield of 77.13%, and (Z)-7-tetradecen-2-yl benzoate (21.54 g, 0.040 mol, purity 59.11%) with a yield of 20.12%.

Thus, by subjecting the remaining unreacted starting materials to benzoation, a difference may be provided between the boiling point of (Z)-7-tetradecen-2-one (5) and the boiling point of (Z)-7-tetradecen-2-yl benzoate, which may be utilized to separate (Z)-7-tetradecen-2-one (5) and (Z)-7-tetradecen-2-yl benzoate by distillation.

The spectrum data of (Z)-7-tetradecen-2-one (5) thus obtained was the same as that of Example 4.

Example 6: Preparation of (Z)-7-tetradecen-2-one (5)

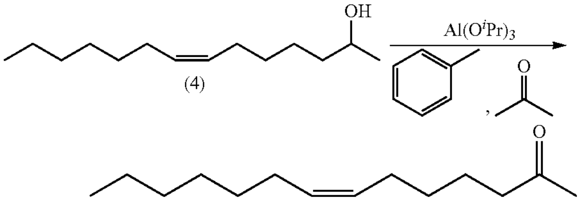

(4)

(5)

(Z)-7-Tetradecen-2-ol (4) (22.32 g, 0.10 mol, purity 95.16%) prepared in Example 3, acetone (227.38 g, 3.91 mol), and toluene (338.75 g) were placed in a reactor at a room temperature and stirred at 75 to 85° C. for 10 minutes. Aluminum triisopropoxide (25.74 g, 0.13 mol) was then dissolved in toluene (169.37 g) and added dropwise at 75 to 80° C. After the completion of the dropwise addition, the mixture was allowed to react at 75 to 85° C. for 24.5 hours, followed by cooling to an internal temperature of 30° C. After the cooling, 20% by mass hydrochloric acid (300.00 g with 1.65 mol of hydrogen chloride) and water (400.00 g) were added, followed by phase separation. The aqueous layer was removed, followed by washing with an aqueous solution of sodium bicarbonate (prepared from sodium bicarbonate (4.0 g) and water (300 g)). The aqueous layer was removed to obtain the organic layer. The organic layer thus obtained was concentrated at a reduced pressure, and the resulting concentrate was distilled at a reduced pressure to obtain 21.85 g of a mixture of (Z)-7-tetradecen-2-one (5) and (Z)-7-tetradecen-2-ol (4). Namely, the mixture thus obtained was (Z)-7-tetradecen-2-one (5) (21.85 g, 0.15 mol, purity 59.18%, b.p.=101.1 to 120.2° C./0.4 kPa (3.0 mmHg)) with a yield of 61.46%, and (Z)-7-tetradecen-2-ol (4) (21.85 g, 0.030 mol, purity 29.39%) with a yield of 30.24%.

(Z)-7-Tetradecen-2-ol (4) and (Z)-7-tetradecen-2-one (5) thus obtained had boiling points near each other, and so separation by distillation was not possible.

The invention claimed is:

1. A process for preparing (Z)-7-tetradecen-2-one of the following formula (5):

(5)

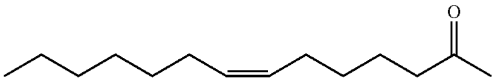

the process comprising the steps of:

converting a (Z)-1-halo-4-undecene compound (1) of the following general formula (1):

(1)

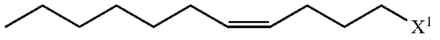

wherein $X^1$ represents a halogen atom, into a nucleophilic reagent, (Z)-4-undecenyl compound, of the following general formula (2):

(2)

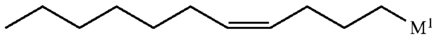

wherein $M^1$ represents Li or $MgZ^1$, and $Z^1$ represents a halogen atom or a (4Z)-4-undecenyl group, subjecting the nucleophilic reagent, (Z)-4-undecenyl compound (2), to an addition reaction with propylene oxide of the following formula (3):

(3)

to obtain (Z)-7-tetradecen-2-ol of the following formula (4):

(4)

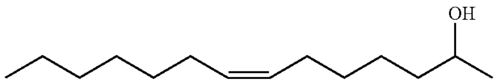

and oxidizing (Z)-7-tetradecen-2-ol (4) thus obtained to form (Z)-7-tetradecen-2-one (5).

2. The process for preparing (Z)-7-tetradecen-2-one (5) according to claim 1, wherein the oxidization is carried out by an Oppenauer oxidation.

3. The process for preparing (Z)-7-tetradecen-2-one (5) according to claim 1, the process further comprising:

esterifying the (Z)-7-tetradecen-2-ol (4) remaining after the aforesaid step of obtaining (Z)-7-tetradecen-2-one (5).

4. The process for preparing (Z)-7-tetradecen-2-one (5) according to claim 3, the process further comprising the step of:

purifying (Z)-7-tetradecen-2-one (5) from a reaction mixture of (Z)-7-tetradecen-2-one (5) and an esterified product of (Z)-7-tetradecen-2-ol (4) after the step of esterification.

5. The process for preparing (Z)-7-tetradecen-2-one (5) according to claim 1, the process further comprising the step of:

subjecting a 1-halo-4-undecyne compound of the following general formula (6):

(6)

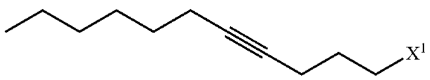

wherein $X^1$ represents a halogen atom, to a reduction reaction to obtain the (Z)-1-halo-4-undecene compound (1).

6. The process for preparing (Z)-7-tetradecen-2-one (5) according to claim 5, the process further comprising the step of:

subjecting a nucleophilic reagent, hexyl compound, of the following general formula (7):

(7)

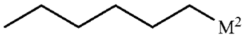

wherein $M^2$ represents Li or $MgZ^2$, and $Z^2$ represents a halogen atom or a hexyl group, to a coupling reaction with a 1,5-dihalo-1-pentyne compound of the following general formula (8):

(8)

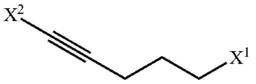

wherein $X^1$ and $X^2$ represent, independently of each other, a halogen atom, to form 1-halo-4-undecyne (6).

7. The process for preparing (Z)-7-tetradecen-2-one (5) according to claim 2, the process further comprising:

esterifying the (Z)-7-tetradecen-2-ol (4) remaining after the aforesaid step of obtaining (Z)-7-tetradecen-2-one (5).

8. The process for preparing (Z)-7-tetradecen-2-one (5) according to claim 7, the process further comprising the step of:

purifying (Z)-7-tetradecen-2-one (5) from a reaction mixture of (Z)-7-tetradecen-2-one (5) and an esterified product of (Z)-7-tetradecen-2-ol (4) after the step of esterification.

9. The process for preparing (Z)-7-tetradecen-2-one (5) according to claim 2, the process further comprising the step of:

subjecting a 1-halo-4-undecyne compound of the following general formula (6):

(6)

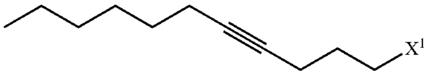

wherein $X^1$ represents a halogen atom, to a reduction reaction to obtain the (Z)-1-halo-4-undecene compound (1).

10. The process for preparing (Z)-7-tetradecen-2-one (5) according to claim 9, the process further comprising the step of:

subjecting a nucleophilic reagent, hexyl compound, of the following general formula (7):

(7)

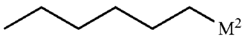

wherein $M^2$ represents Li or $MgZ^2$, and $Z^2$ represents a halogen atom or a hexyl group, to a coupling reaction with a 1,5-dihalo-1-pentyne compound of the following general formula (8):
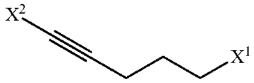
(8)
wherein $X^1$ and $X^2$ represent, independently of each other, a halogen atom,
to form 1-halo-4-undecyne (6).
* * * * *